United States Patent
Bonnette et al.

(10) Patent No.: US 8,157,766 B2
(45) Date of Patent: Apr. 17, 2012

(54) TORQUEABLE KINK-RESISTANT GUIDEWIRE

(75) Inventors: Michael J. Bonnette, Minneapolis, MN (US); Richard R. Prather, St. Michael, MN (US); Eric J. Thor, Arden Hills, MN (US)

(73) Assignee: MEDRAD, Inc., Indianola, PA (US)

( * ) Notice: Subject to any disclaimer, the term of this patent is extended or adjusted under 35 U.S.C. 154(b) by 574 days.

(21) Appl. No.: 12/368,578

(22) Filed: Feb. 10, 2009

(65) Prior Publication Data
US 2009/0143729 A1 Jun. 4, 2009

Related U.S. Application Data

(62) Division of application No. 11/217,545, filed on Sep. 1, 2005, now abandoned.

(51) Int. Cl.
*A61M 29/00* (2006.01)

(52) U.S. Cl. ............. 604/96.01; 604/103.09; 604/103.1; 600/585; 606/192

(58) Field of Classification Search ............... 604/96.01, 604/99.01–99.04, 103.09, 103.1; 600/585; 606/192, 194
See application file for complete search history.

(56) References Cited

U.S. PATENT DOCUMENTS

| | | | |
|---|---|---|---|
| 3,773,290 A | 11/1973 | Mowery |
| 4,122,556 A | 10/1978 | Poler |
| 4,166,807 A | 9/1979 | Komatsu et al. |
| 4,332,254 A | 6/1982 | Lundquist |
| 4,467,003 A | 8/1984 | Pallaroni et al. |
| 4,545,390 A | 10/1985 | Leary |
| 4,554,929 A | 11/1985 | Samson |
| 4,573,470 A | 3/1986 | Samson et al. |
| 4,573,966 A | 3/1986 | Weikl et al. |
| 4,583,974 A | 4/1986 | Kokernak |
| 4,636,195 A | 1/1987 | Wolinsky |
| 4,646,719 A | 3/1987 | Neuman et al. |
| 4,651,738 A | 3/1987 | Demer et al. |
| 4,653,539 A | 3/1987 | Bell |
| 4,690,672 A | 9/1987 | Veltrup |
| 4,719,924 A | 1/1988 | Crittenden |
| 4,723,938 A | 2/1988 | Goodin |
| 4,733,652 A | 3/1988 | Kantrowitz et al. |

(Continued)

FOREIGN PATENT DOCUMENTS

EP 1278570 10/2006

(Continued)

OTHER PUBLICATIONS

Glidewire Gold Hydrophilic Coated Guidewires, Terumo Medical Corporation, (www.terumois.com website), as early as 2008.

(Continued)

*Primary Examiner* — Theodore Stigell
(74) *Attorney, Agent, or Firm* — James R. Stevenson; David Schramm

(57) ABSTRACT

An occlusive guidewire system having an ergonomic hand-held control mechanism and torqueable kink-resistant guidewire having a distally located inflatable balloon. The present invention provides convenient structure and overall mechanism for operation of a torqueable kink-resistant guidewire, including evacuation and inflation control of an occlusive balloon, and sealing and severing of a crimpable inflation tube which is in communication with an occlusive balloon. The torqueable kink-resistant guidewire includes a centrally located shaft which imparts robustness to the torqueable kink-resistant guidewire. An inflation lumen aligns within the torqueable kink-resistant guidewire for inflation of the balloon.

33 Claims, 12 Drawing Sheets

U.S. PATENT DOCUMENTS

| | | | |
|---|---|---|---|
| 4,757,827 A | 7/1988 | Buchbinder | |
| 4,758,223 A | 7/1988 | Rydell | |
| 4,795,431 A | 1/1989 | Walling | |
| 4,800,890 A | 1/1989 | Cramer | |
| 4,832,023 A | 5/1989 | Murphy-Chutorian et al. | |
| 4,838,268 A | 6/1989 | Keith et al. | |
| 4,846,174 A | 7/1989 | Willard | |
| 4,858,810 A | 8/1989 | Intlekofer et al. | |
| 4,865,587 A | 9/1989 | Walling | |
| 4,886,067 A | 12/1989 | Palermo | |
| 4,906,241 A | 3/1990 | Noddin | |
| 4,925,445 A | 5/1990 | Sakamoto | |
| 4,943,278 A | 7/1990 | Euteneuer | |
| 4,946,466 A | 8/1990 | Pinchuk | |
| 4,955,384 A | 9/1990 | Taylor | |
| 5,014,494 A | 5/1991 | George | |
| 5,019,041 A | 5/1991 | Robinson | |
| 5,035,686 A | 7/1991 | Cittendan | |
| 5,059,176 A | 10/1991 | Winters | |
| 5,059,178 A | 10/1991 | Ya | |
| 5,069,226 A | 12/1991 | Yamauchi et al. | |
| 5,106,363 A | 4/1992 | Nobuyoshi | |
| RE33,911 E | 5/1992 | Samson | |
| 5,120,308 A | 6/1992 | Hess | |
| 5,135,482 A | 8/1992 | Neracher | |
| 5,135,484 A | 8/1992 | Wright | |
| 5,139,032 A | 8/1992 | Jahrmarkt | |
| 5,147,300 A | 9/1992 | Robinson | |
| 5,163,904 A | 11/1992 | Lampropoulos | |
| 5,167,239 A | 12/1992 | Cohen et al. | |
| 5,171,221 A | 12/1992 | Samson | |
| 5,176,692 A | 1/1993 | Wilk et al. | |
| 5,195,955 A | 3/1993 | Don Michael | |
| 5,196,245 A | 3/1993 | DeRudder et al. | |
| 5,207,656 A | 5/1993 | Kranys | |
| 5,209,727 A | 5/1993 | Radisch, Jr. et al. | |
| 5,259,838 A | 11/1993 | Taylor | |
| 5,261,877 A | 11/1993 | Fine | |
| 5,320,604 A | 6/1994 | Walker et al. | |
| 5,324,260 A | 6/1994 | O'Neill et al. | |
| 5,334,153 A | 8/1994 | McIntyre et al. | |
| 5,338,301 A | 8/1994 | Diaz | |
| 5,380,284 A | 1/1995 | Don Michael | |
| 5,399,658 A | 3/1995 | Archey et al. | |
| 5,411,033 A | 5/1995 | Viera | |
| 5,411,476 A | 5/1995 | Abrams | |
| 5,413,581 A | 5/1995 | Goy | |
| 5,429,139 A | 7/1995 | Sauter | |
| 5,429,606 A | 7/1995 | Robinson | |
| 5,437,288 A | 8/1995 | Schwartz | |
| 5,443,907 A * | 8/1995 | Slaikeu et al. | 428/375 |
| 5,449,343 A | 9/1995 | Samson | |
| 5,472,424 A | 12/1995 | Lampropoulos | |
| 5,474,194 A | 12/1995 | Heilman et al. | |
| 5,490,837 A | 2/1996 | Blaeser | |
| 5,505,699 A | 4/1996 | Forman et al. | |
| 5,514,109 A | 5/1996 | Mollenauer et al. | |
| 5,520,645 A | 5/1996 | Imran et al. | |
| 5,536,242 A | 7/1996 | Willard | |
| 5,558,643 A | 9/1996 | Samson | |
| 5,569,197 A | 10/1996 | Helmus | |
| 5,573,520 A | 11/1996 | Schwartz | |
| 5,583,047 A | 12/1996 | Blinka et al. | |
| 5,584,843 A | 12/1996 | Wulfman et al. | |
| 5,601,539 A | 2/1997 | Corso | |
| 5,605,162 A | 2/1997 | Mirzaee | |
| 5,624,396 A | 4/1997 | McNamara | |
| 5,647,847 A | 7/1997 | Lafontaine | |
| 5,685,848 A | 11/1997 | Robinson | |
| 5,688,234 A | 11/1997 | Frisbie | |
| 5,697,380 A | 12/1997 | Quiachon | |
| 5,704,912 A | 1/1998 | Lawrence | |
| 5,713,917 A | 2/1998 | Leonhardt et al. | |
| 5,728,064 A | 3/1998 | Burns | |
| 5,741,229 A | 4/1998 | Robinson | |
| 5,752,935 A | 5/1998 | Robinson | |
| 5,775,327 A | 7/1998 | Randolph et al. | |
| 5,776,100 A | 7/1998 | Forman | |
| 5,779,672 A | 7/1998 | Dormandy | |
| 5,779,688 A | 7/1998 | Imran et al. | |
| 5,779,721 A | 7/1998 | Nash | |
| 5,792,179 A | 8/1998 | Sideris | |
| 5,794,325 A | 8/1998 | Fallandy | |
| 5,795,325 A | 8/1998 | Valley et al. | |
| 5,807,330 A | 9/1998 | Teitelbaum | |
| 5,820,613 A | 10/1998 | Vam Wevenranseen | |
| 5,827,201 A | 10/1998 | Samson | |
| 5,827,324 A | 10/1998 | Cassell et al. | |
| 5,833,644 A | 11/1998 | Zadno-Azizi et al. | |
| 5,833,650 A | 11/1998 | Imran | |
| 5,843,022 A | 12/1998 | Willard et al. | |
| 5,851,203 A | 12/1998 | Van Muiden | |
| 5,853,408 A | 12/1998 | Muni | |
| 5,861,003 A | 1/1999 | Latson | |
| 5,865,721 A | 2/1999 | Andrews et al. | |
| 5,868,705 A | 2/1999 | Bagaoisan | |
| 5,879,361 A | 3/1999 | Nash | |
| 5,881,534 A | 3/1999 | Ahlqvist et al. | |
| 5,893,867 A | 4/1999 | Bagaoisan | |
| 5,908,405 A | 6/1999 | Imran et al. | |
| 5,916,178 A | 6/1999 | Noone | |
| 5,925,016 A | 7/1999 | Chornenky et al. | |
| 5,938,623 A | 8/1999 | Quiachon | |
| 5,938,672 A | 8/1999 | Nash | |
| 5,980,471 A | 11/1999 | Jafari | |
| 5,997,558 A | 12/1999 | Nash | |
| 5,997,562 A | 12/1999 | Zadno-Azizi | |
| 6,004,279 A | 12/1999 | Crowley | |
| 6,017,319 A | 1/2000 | Jacobsen | |
| 6,021,340 A | 2/2000 | Randolph et al. | |
| 6,022,336 A | 2/2000 | Zadno-Azizi et al. | |
| 6,036,715 A | 3/2000 | Yock | |
| 6,039,743 A | 3/2000 | Quiachon | |
| 6,050,972 A | 4/2000 | Zadno-Azizi et al. | |
| 6,068,623 A | 5/2000 | Zadno-Azizi | |
| 6,071,273 A | 6/2000 | Euteneuer | |
| 6,080,170 A | 6/2000 | Nash et al. | |
| 6,090,083 A | 7/2000 | Sell | |
| 6,102,931 A | 8/2000 | Thornton | |
| 6,110,142 A | 8/2000 | Pinchuk | |
| 6,123,698 A | 9/2000 | Spears et al. | |
| 6,135,991 A | 10/2000 | Muni et al. | |
| 6,139,510 A | 10/2000 | Palermo | |
| 6,146,339 A | 11/2000 | Biagtan | |
| 6,146,372 A | 11/2000 | Leschinsky et al. | |
| 6,152,909 A | 11/2000 | Bagaoisan | |
| 6,156,054 A | 12/2000 | Zadno-Azizi | |
| 6,159,195 A | 12/2000 | Ha | |
| 6,161,695 A | 12/2000 | Nicolais | |
| 6,166,116 A | 12/2000 | Sleeckx | |
| 6,171,328 B1 | 1/2001 | Addis | |
| 6,176,844 B1 | 1/2001 | Lee | |
| 6,190,354 B1 | 2/2001 | Sell et al. | |
| 6,203,561 B1 | 3/2001 | Ramee et al. | |
| 6,217,567 B1 | 4/2001 | Zadno-Azizi et al. | |
| 6,224,570 B1 | 5/2001 | Le et al. | |
| 6,231,588 B1 | 5/2001 | Zadno-Azizi | |
| 6,234,996 B1 | 5/2001 | Bagaoisan et al. | |
| 6,241,706 B1 | 6/2001 | Leschinsky et al. | |
| 6,241,744 B1 | 6/2001 | Imran et al. | |
| 6,245,008 B1 | 6/2001 | Leschinsky et al. | |
| 6,245,089 B1 | 6/2001 | Daniel et al. | |
| 6,251,093 B1 | 6/2001 | Valley et al. | |
| 6,355,016 B1 | 3/2002 | Bagaoisan et al. | |
| 6,464,664 B1 | 10/2002 | Jonkman et al. | |
| 6,471,671 B1 | 10/2002 | Urick et al. | |
| 6,475,185 B1 | 11/2002 | Rauker et al. | |
| 6,485,657 B1 | 11/2002 | Funakoshi et al. | |
| 6,494,314 B1 | 12/2002 | Lamborne et al. | |
| 6,517,518 B2 | 2/2003 | Nash et al. | |
| 6,524,323 B1 | 2/2003 | Nash et al. | |
| 6,544,276 B1 | 4/2003 | Azizi | |
| 6,565,527 B1 | 5/2003 | Jonkman et al. | |
| 6,569,147 B1 | 5/2003 | Evans et al. | |
| 6,569,151 B1 | 5/2003 | Nash et al. | |
| 6,652,546 B1 | 11/2003 | Nash et al. | |
| 6,743,208 B1 | 6/2004 | Coyle | |

| | | |
|---|---|---|
| 6,830,577 B2 | 12/2004 | Nash et al. |
| 6,843,797 B2 | 1/2005 | Nash et al. |
| 6,869,417 B1 | 3/2005 | Walters et al. |
| 6,872,192 B2 | 3/2005 | Nash et al. |
| 6,902,535 B2 | 6/2005 | Eberhart et al. |
| 6,905,505 B2 | 6/2005 | Nash et al. |
| 6,927,063 B2 | 8/2005 | Moreton et al. |
| 6,932,828 B2 | 8/2005 | Bonnette et al. |
| 6,936,056 B2 | 8/2005 | Nash et al. |
| 6,942,678 B2 | 9/2005 | Bonnette et al. |
| 6,962,707 B2 | 11/2005 | Schenk |
| 6,966,903 B2 | 11/2005 | Jonkman et al. |
| 7,004,914 B2 | 2/2006 | Eberhart et al. |
| 7,048,696 B2 | 5/2006 | Eberhart et al. |
| 7,169,161 B2 | 1/2007 | Bonnette et al. |
| 7,219,799 B2 | 5/2007 | Bonnette et al. |
| 7,220,243 B2 | 5/2007 | Bonnette et al. |
| 7,226,425 B2 | 6/2007 | Eberhart et al. |
| 7,316,678 B2 | 1/2008 | Nash et al. |
| 7,334,681 B2 | 2/2008 | Bonnette et al. |
| 7,367,982 B2 | 5/2008 | Nash et al. |
| 2001/0014821 A1 | 8/2001 | Juman et al. |
| 2001/0016704 A1 | 8/2001 | Zadno-Azizi et al. |
| 2002/0096521 A1 | 7/2002 | Cardarelli |
| 2003/0088194 A1* | 5/2003 | Bonnette et al. .............. 600/585 |
| 2003/0088262 A1 | 5/2003 | Bonnette et al. |
| 2003/0088263 A1 | 5/2003 | Bonnette et al. |
| 2003/0208134 A1 | 11/2003 | Secrest et al. |
| 2004/0031721 A1 | 2/2004 | Mann |
| 2004/0039304 A1 | 2/2004 | Connors, III et al. |
| 2004/0039306 A1 | 2/2004 | Eberhart et al. |
| 2004/0039310 A1 | 2/2004 | Burkett |
| 2004/0050740 A1 | 3/2004 | Lewis |
| 2004/0059284 A1 | 3/2004 | Nash et al. |
| 2004/0097995 A1 | 5/2004 | Nash et al. |
| 2004/0133185 A1 | 7/2004 | Nash et al. |
| 2004/0210164 A1 | 10/2004 | Eberhart et al. |
| 2005/0020998 A1 | 1/2005 | Bonnette et al. |
| 2005/0075647 A1 | 4/2005 | Walters et al. |
| 2005/0080357 A1 | 4/2005 | Eberhart et al. |
| 2005/0182437 A1 | 8/2005 | Bonnette et al. |
| 2007/0060878 A1 | 3/2007 | Bonnette |
| 2007/0060881 A1 | 3/2007 | Bonnette et al. |
| 2008/0097298 A1 | 4/2008 | Fisher |

FOREIGN PATENT DOCUMENTS

| | | |
|---|---|---|
| WO | WO0215971 | 2/2002 |
| WO | WO0224271 | 3/2002 |
| WO | WO02094364 | 11/2002 |
| WO | WO2004018032 | 3/2004 |
| WO | WO2004028592 | 4/2004 |

OTHER PUBLICATIONS

"The Probe, A Balloon-on-the-Wire", Texas Heat Institute Journal, 1989; 16:95-101.
TriActiv System, Kensey Nash (www.kenseynash.com website), as early as 2003.
EP Search Report of related application dated Apr. 6, 2011.
U.S. Appl. No. 10/930,528, filed Aug. 31, 2004, "Low Pierce Force Needle Port", Bonnette.
Exam Report dated Aug. 6, 2007 in corresponding EP 02784406.
Search Report dated May 8, 2008 in corresponding PCT/US07/22023.
Search Report dated Oct. 29, 2007 in corresponding WO65425.
Search Report dated Jun. 12, 2008 in corresponding WO0815724.
Search Report dated Jun. 4, 2004 in corresponding WO03039624.
Search Report dated Feb. 27, 2007 in corresponding WO05110523.
Search Report dated Mar. 29, 2006 in corresponding WO05110524.
Search Report dated Sep. 26, 2007 in corresponding WO07027563.

* cited by examiner

TORQUEABLE KINK-RESISTANT GUIDEWIRE

CROSS REFERENCES TO RELATED APPLICATIONS

This application for patent claims the benefit of U.S. application Ser. No. 11/217,545, filed 1 Sep. 2005. This patent application is also related to application Ser. No. 10/838,464 entitled "Gas Inflation/Evacuation System and Sealing System Incorporating a Compression Sealing Mechanism for Guidewire Assembly Having Occlusive Device" filed on May 4, 2004, and application Ser. No. 10/838,468 entitled "Guidewire Assembly Including a Repeatably Inflatable Occlusive Balloon on a Guidewire Ensheathed with a Spiral Coil" filed on May 4, 2004, both of which are continuations-in-part of application Ser. Nos. 10/012,903, 10/012,891 and 10/007,788 all filed on Nov. 6, 2001.

BACKGROUND OF THE INVENTION

1. Field of the Invention

The present invention relates to medical devices, but more directly relates to devices utilized to provide for temporary occlusion in the vasculature during surgical procedures.

2. Description of the Prior Art

Prior art devices incorporated inflation of balloons to provide for temporary occlusions in the vasculature, whereby an inflatable balloon attached to the distal end of a guidewire having an internal inflation lumen is inflated. Such a device is useful during cross stream thrombectomy procedures where the guidewire having an internal inflation lumen can be used as an ordinary guidewire. Alternatively, such a device can also be useful to prevent downstream distribution of lysins beyond a region of thrombus or other undesirable buildup. The structure of the prior art devices incorporated to operate the guidewire having an internal inflation lumen often included a collection of multiple components coupled together to provide for connection of multiple tubes, valves, syringes, connectors and other associated components. Often the assembled collection of components proved to be of an unwieldy nature and often was cumbersome to use. In addition to the user unfriendly aspects of the prior art devices, other problems were encountered when aligning the guidewire having an internal inflation lumen in the vasculature. Due to the small size of the guidewire with a lumen and due to the lack of robustness, undesirable kinking and bending of the guidewire occurred when positioning the guidewire along the vasculature. Such undesirable kinking and bending also occurred when the guidewire having a lumen was torqued or twisted about its flexible longitudinal axis in order to steer a flexible tip along tortuous paths of the vasculature. The present invention, an occlusive guidewire system having an ergonomic handheld control mechanism and torqueable kink-resistant guidewire, overcomes the inadequacies of the prior art devices.

SUMMARY OF THE INVENTION

The general purpose of the present invention is to provide an occlusive guidewire system having an ergonomic handheld control mechanism and torqueable kink-resistant guidewire.

The handheld control mechanism incorporates upper and lower housing halves about an internal mechanism assembly having a compression sealing mechanism, an inflation tube sealing mechanism, an inflation syringe, an evacuation syringe, inflation and evacuation control valves, a pressure gauge, and a plurality of other components. The handheld control mechanism is ergonomically designed and shaped to provide for easy and efficient operation during medical procedures, as well as to provide convenient housing of components. The torqueable and kink-resistant guidewire, the proximal end of which is accommodated by the handheld control mechanism, includes an inflatable occlusive device preferably in the form of a balloon which is distally located thereupon.

This invention relates to the balloon occlusive/distal protection guidewire technology and functions like other guidewires having distally located inflatable occlusive devices that are already being produced, i.e., $CO_2$ filled balloons that utilize a special crimping/inflation device to seal them and make them hubless to be used as an ordinary guidewire. This invention relates to an enhancement to the existing technology.

The torqueable kink-resistant guidewire includes a balloon which is inflatable and which is deflatable and a flexible tip located at or near a distal location along the guidewire. The torqueable kink-resistant guidewire consists primarily of a shaft, a crimpable inflation tube which is molded into the guidewire structure or which could fit full length or in segmented lengths in the gas conduit, a balloon, a coated polymer jacket, and a guidewire tip. The shaft is embedded centrally within the torqueable kink-resistant guidewire and is tapered and can be preshaped at the distal end to provide for appropriate transition to the guidewire tip to allow for the device to behave like an ordinary guidewire, i.e., the transition is important to how the guidewire traverses through the vasculature of the body without damage. Ordinarily, the shaft is made of nitinol, which provides the kink resistance to the device due to its super elastic properties, and the torqueability of the device since it transfers proximal rotational force to the distal section in a one-to-one fashion because of the physical structure of the device, i.e., a solid rod of appropriate dimension in conjunction with a polymer jacket of fairly rigid plastic that is firmly attached to the rod will display this characteristic. Torque response is a necessity in guiding the guidewire through torturous vasculature. The gas inflation tube by itself or with other combinations involving the conduit transfers gas from the inflation structure in the handheld control mechanism to the distal balloon. The gas inflation tube could be a physical tube (metal, plastic or composite) or it could be formed within the device via a mandrel or a specifically shaped nitinol shaft. The proximal section of the inflation tube is designed to have crimpable attributes such that portions thereof can be repeatably sealed via the inflation tube sealing mechanism, a special crimping device. The sealed proximal end can be removed from the inflation tube sealing mechanism of the handheld control mechanism so that the wire can be used like an ordinary guidewire as a hubless system (see previous patents and disclosures of the assignee for crimping/inflation device design). The crimpable inflation tube needs to be of a specific dimension, material, and hardness to be compatible with the inflation tube sealing mechanism, such as metal with a medium hardness. The balloon can be made from many different materials that may be noncompliant, semi-compliant, or compliant, such as silicone, Pebax, or polyurethane. The purpose of the balloon is to occlude flow to prevent distal embolization of particles (which cause more damage), to minimize hemolytic components or drugs from flowing throughout the body, to contain other agents, to center another device within the vessel, or to provide for an isolated environment within a vessel. The polymer jacket can be coated, such as with a hydrophilic coating, to improve trackability or compatibility with other interventional devices, or uncoated depending on the polymer used and the use and required performance of the guidewire. The polymer can be any type of polymer, but most preferably one that is flexible enough to allow for appropriate guidewire structure, and one that is rigid enough to aid in torqueability. It is also preferred to have this polymer loaded with a radiopaque material, such as tungsten or $BaSO_4$ (barium sulfate), to improve the visibility of the device under normal fluoroscopy. The guidewire tip usually consists of a core and, alternatively, an outer coil or a polymer jacket. The design of the guidewire tip is important such that it allows the device to be steered and placed in the damaged vasculature.

According to one or more embodiments of the present invention, there is provided an occlusive guidewire system having a handheld control mechanism and torqueable kink-resistant guidewire where the handheld control mechanism includes, but is not limited to, an upper housing half and a lower housing half whereat a plurality of components included in an internal mechanism assembly secure to, within or thereabout, including an inflation syringe, an evacuation syringe, an inline inflation control valve and actuator button, an inline evacuation control valve and actuator button, an inflation tube sealing mechanism, a compression sealing mechanism, a pressure gauge, a four-port infusion "y", and where the torqueable kink-resistant guidewire includes, but is not limited to, a centrally located nitinol shaft having a polymer jacket, such jacket extending along and about a greater portion of the nitinol shaft, along and about a portion of the crimpable inflation tube where the distal end of the inflation tube extends to communicate with a balloon located at the distal end of the nitinol shaft, and where the inflation tube proximal end extends proximally beyond the polymer jacket and nitinol shaft, and a distally located flexible tip.

One significant aspect and feature of the present invention is an occlusive guidewire system having an ergonomic handheld control mechanism and torqueable kink-resistant guidewire.

Another significant aspect and feature of the present invention is an ergonomic handheld control mechanism which conveniently contains mounted components essential to the operation of a torqueable kink-resistant guidewire assembled for minimizing problems encountered in freeform and unrestrained arrangements where components are not secured for efficient and useful operation thereof.

Another significant aspect and feature of the present invention is an ergonomic handheld control mechanism having simple lineally actuated control valves being readily accessible by the operator as opposed to rotary valves incorporated in other arrangements.

Yet another significant aspect and feature of the present invention is an ergonomic handheld control mechanism having lineally actuated control valves aligned within arcuate recesses to allow only wanted actuation and to prevent inadvertent control valve actuation.

Still another significant aspect and feature of the present invention is an ergonomic handheld control mechanism having a built-in and mounted pressure gauge.

Another significant aspect and feature of the present invention is an ergonomic handheld control mechanism having a built-in and mounted inflation tube sealing mechanism and a compression sealing mechanism.

A further significant aspect and feature of the present invention is an ergonomic handheld control mechanism having a built-in and mounted evacuation syringe and inflation syringe.

Another significant aspect and feature of the present invention is an ergonomic handheld control mechanism having built-in and mounted check valves.

In addition to the above, significant aspects and features of the present invention also involve a torqueable kink-resistant guidewire, wherein:

1. the kink-resistant torqueable guidewire with distal balloon employs crimpable/sealable structure that allows other devices to be passed over it while the balloon is inflated, i.e., a hubless balloon guidewire;
2. the kink-resistant torqueable guidewire with distal balloon uses gas (such as $CO_2$, argon, or helium) as an inflation medium;
3. the kink-resistant torqueable guidewire with distal balloon is polymer jacketed and radiopaque, such as in the use of a tungsten or barium sulfate filled polyurethane;
4. the kink-resistant torqueable guidewire with distal balloon is coated with a hydrophilic material to give ultra lubricity;
5. the kink-resistant torqueable guidewire with distal balloon uses a conduit or inflation lumen along the entire length and ending under an attached balloon to transfer pressurized inflation gas to the balloon which is constructed by any of the means described above;
6. the kink-resistant torqueable guidewire with distal balloon employs nitinol or another super-elastic material as the inner shaft or core that makes the device kink resistant;
7. the kink-resistant torqueable guidewire with distal balloon has either a shapeable coiled tip, a preshaped coil tip, a preshaped polymer tip, or a shapeable polymer tip;
8. the kink-resistant torqueable guidewire with distal balloon uses compliant, semi-compliant, or noncompliant polymer balloons, such as polyurethane, Pebax, silicone, poly-isoprene, C-flex, latex, and the like;
9. the kink-resistant torqueable guidewire with distal balloon is constructed in the previously described alternative ways;
10. the kink-resistant torqueable guidewire with distal balloon is used for distal protection with Angiojete (cross stream thrombectomy) catheters or other aspiration systems to remove the trapped particles;
11. the kink-resistant torqueable guidewire with distal balloon is used as part of an isolation system for purposes of hemolysin containment or drug infusion that may or may not include a proximal protection device;
12. the kink-resistant torqueable guidewire with distal balloon is used for embolectomy with or without an aspiration system;
13. the kink-resistant torqueable guidewire with distal balloon incorporates a spiral cut tube to provide for communication between a crimpable inflation tube, along a conduit or inflation lumen, and a distally located balloon; and,
14. the kink-resistant torqueable guidewire with distal balloon is useful as a centering device for other devices, such as Angiojet®.

Having thus briefly described the present invention and having mentioned some significant aspects and features of the present invention, it is the principal object of the present invention to provide an occlusive guidewire system having an ergonomic handheld control mechanism and torqueable kink-resistant guidewire.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
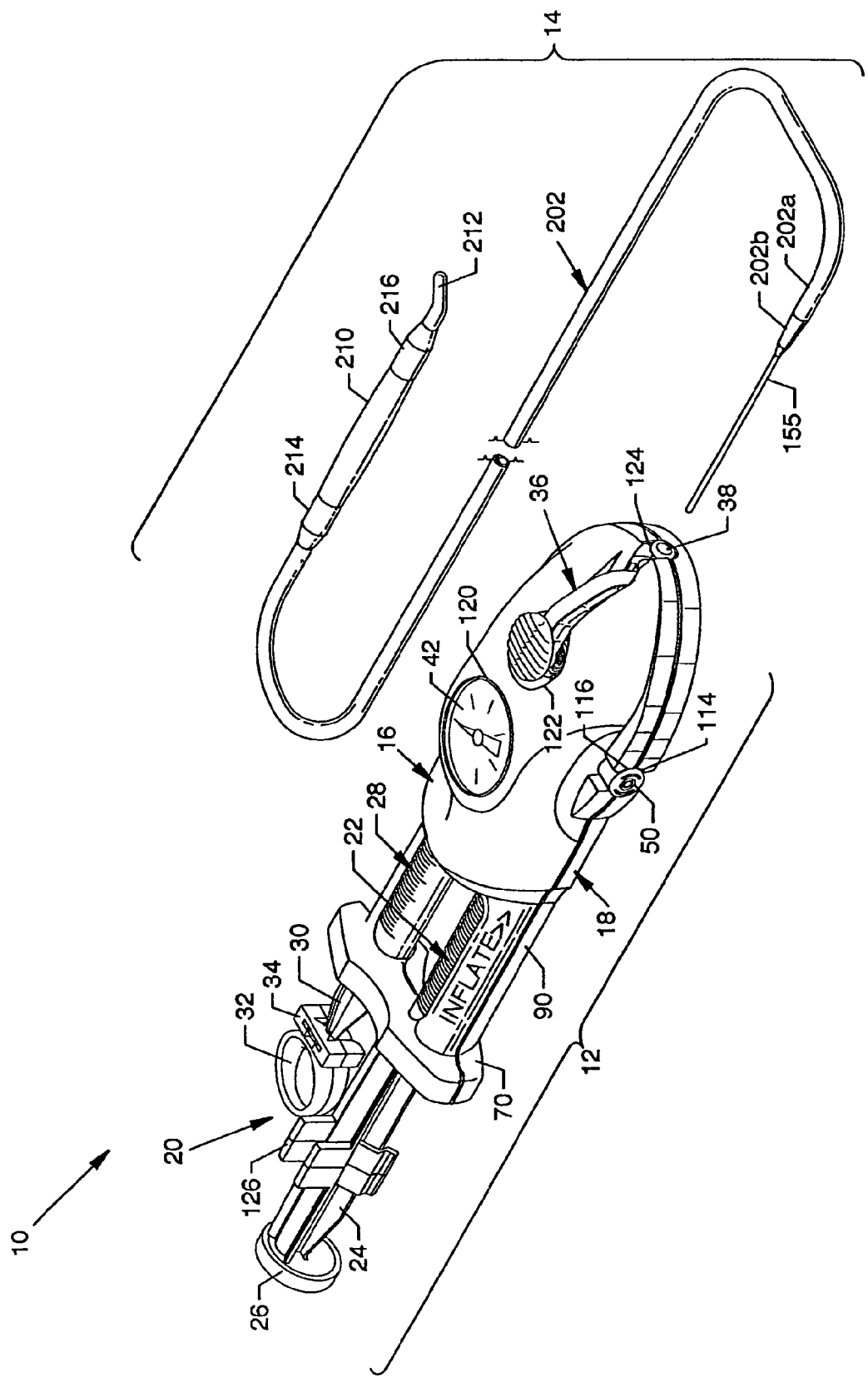
FIG. 1 is an isometric view of an occlusive guidewire system having an ergonomic handheld control mechanism and torqueable kink-resistant guidewire, the present invention.
Figure 2:
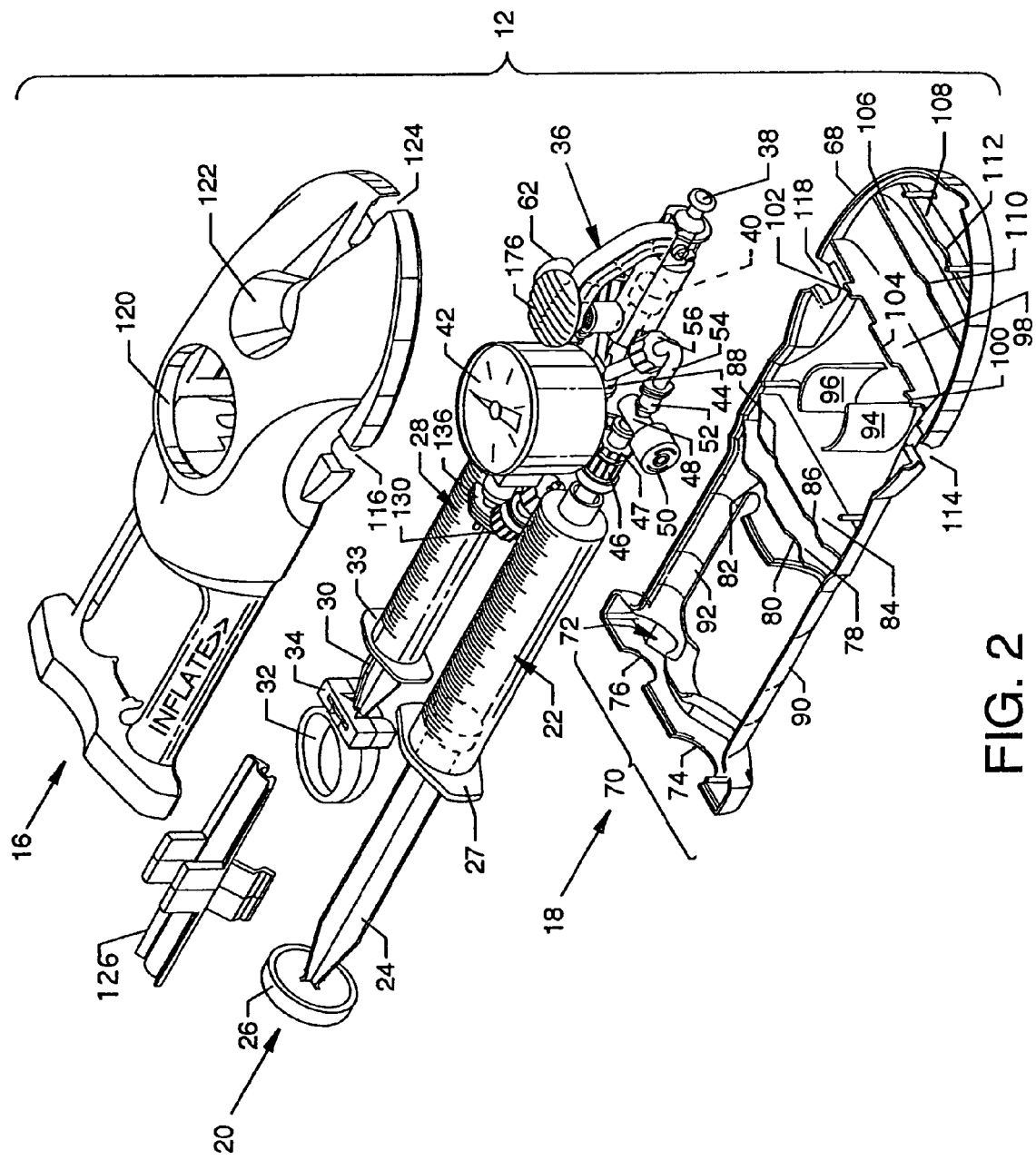
FIG. 2 is an exploded isometric view of the handheld control mechanism of FIG. 1.

FIG. 1 is an isometric view of an occlusive guidewire system having an ergonomic handheld control mechanism and torqueable kink-resistant guidewire 10, the present invention, including a handheld control mechanism 12 and a torqueable kink-resistant guidewire 14, and FIG. 2 is an exploded isometric view of the handheld control mechanism 12 of FIG. 1. With reference to FIGS. 1 and 2, the present invention is now described. The handheld control mechanism 12 is ergonomically shaped, including an ergonomically shaped upper housing half 16 and an ergonomically shaped lower housing half 18, which together encompass and serve as mounting structure for full or partial encasement of the majority of the components included in a centrally located internal mechanism assembly 20. Components of the internal mechanism assembly 20, as also shown in FIGS. 2 and 3, include a graduated inflation syringe 22 having a plunger 24, an actuator pad 26 and a flange 27, a graduated evacuation syringe 28 having a plunger 30, an actuator ring 32, a flange 33, a plunger stop 34, an inflation tube sealing mechanism 36 including a receptor orifice 38, a compression sealing mechanism 40 (FIG. 5) intimately engaging the inflation tube sealing mechanism 36, and a pressure gauge 42 preferably calibrated in atmosphere units (ATM).

Figure 3:
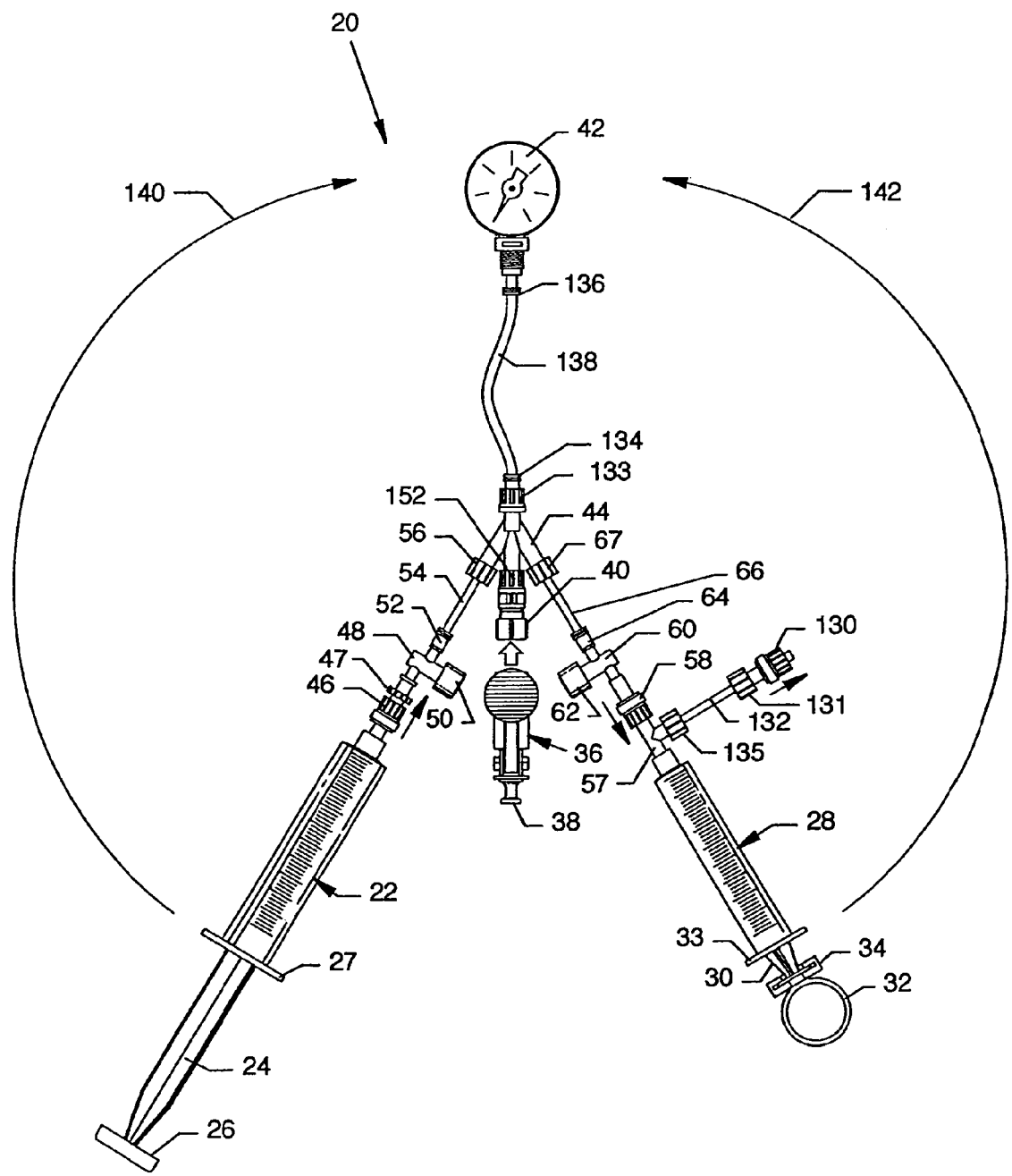
FIG. 3 is a view of the internal mechanism assembly prior to installation between the upper housing half and the lower housing half of the handheld control mechanism.

Also included and as shown in FIG. 3 is the distal end of the inflation syringe 22 connecting to a four-port infusion "Y" 44 using a Luer connector check valve 46, a female-to-female Luer coupler 47, an inline inflation control valve 48 having an inflation control valve actuator button 50, a female slip Luer 52, a flexible plastic tube 54, and a Luer connector 56.

In a similar manner and as shown in FIG. 3 is the distal end of the evacuation syringe 28 connecting to the four-port infusion "Y" 44 using a female Luer lock tee 57, a Luer connector check valve 58, an inline evacuation control valve 60 having an evacuation control valve actuator button 62, a female slip Luer 64, a flexible plastic tube 66, and a Luer connector 67.

The inflation control valve 48 and the evacuation control valve 60 are inline valves which are normally closed to maintain a closed valve position. Depressing the inflation control valve actuator button 50 of the inflation control valve 48 or depressing the evacuation control valve actuator button 62 of the evacuation control valve 60 causes opening of the respective valve to allow passage therethrough, and releasing the inflation control valve actuator button 50 of the inflation control valve 48 or releasing the evacuation control valve actuator button 62 of the evacuation control valve 60 causes each respective valve to automatically return to the closed position.

The ergonomically shaped upper housing half 16 and ergonomically shaped lower housing half 18 encompass and serve as mounting structure for full or partial support or encasement of the majority of the components of the centrally located internal mechanism assembly 20. The mounting or containment structure of the upper housing half 16 for the most part contains corresponding and accommodating structure and functions much in the same manner as that of the lower housing half 18 for securing components of the internal mechanism assembly 20 in place against the geometry of the lower housing half 18, but is not shown for the purpose of brevity.

Figure 4:
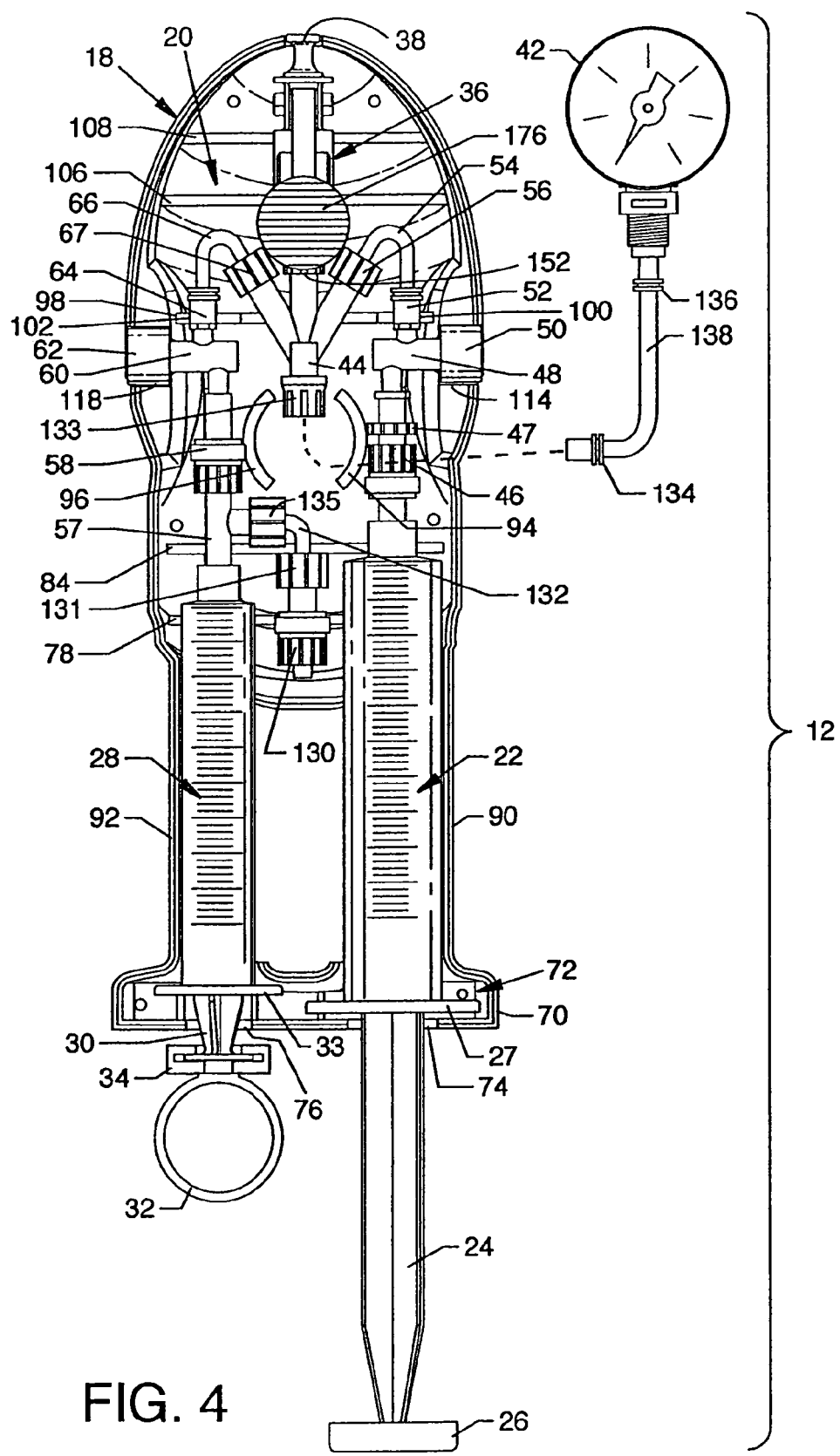
FIG. 4 is a view of the internal mechanism assembly installed in the lower housing half.

The lower housing half 18 is bounded by a segmented mating edge 68 and has structure for mounting of the inflation syringe 22 and the evacuation syringe 28. Such structure includes a syringe support bracket 70 characterized by a laterally oriented channel 72 having arcuate notches 74 and 76 for partially accommodating the plungers 24 and 30. The channel 72 also accommodatingly captures lower portions of the flanges 27 and 33 of the inflation syringe 22 and the evacuation syringe 28, respectively, as shown in FIG. 4. A laterally oriented syringe support bar 78 having arcuate notches 80 and 82 along the top edge, and a laterally oriented syringe support bar 84 having arcuate notches 86 and 88 along the top edge and being parallel to the syringe support bar 78, span the lower housing half 18 to offer support of the distal portions of the inflation syringe 22 and the evacuation syringe 28, respectively. Longitudinally oriented arcuate extensions 90 and 92 connect the syringe support bracket 70 to the main body of the lower housing half 18. Vertically oriented arcuate tabs 94 and 96 extend from the main body of the lower housing half 18 to assist in support of the pressure gauge 42. Another laterally oriented support bar 98 having elevated arcuate notches 100 and 102 provides support for the female slip Luer 52 and the female slip Luer 64 (FIG. 3), as well as a center support 104 for support of the four-port infusion "Y" 44. Laterally oriented support bars 106 and 108 having arcuate notches 110 and 112, respectively, are provided for support of the inflation tube sealing mechanism 36.

Structure is also provided for accommodation of the inflation and evacuation control valve actuator buttons 50 and 62 in the form of notches about the edges of the upper housing half 16 and the lower housing half 18. In the lower housing half 18 an interrupted arcuate notch 114 is provided. The interrupted arcuate notch 114 includes a radius slightly larger than the radius of the inflation control valve actuator button 50, whereby the slightly larger radius of the interrupted arcuate notch 114 provides for guided near tangential close spaced support of the inflation control valve actuator button 50. In the upper housing half 16 a corresponding and mating interrupted arcuate notch 116 is also provided to provide a function similar to that of the interrupted arcuate notch 114. Correspondingly, on the lower housing half 18 an interrupted arcuate notch 118 opposes the interrupted arcuate notch 114 and mates to another interrupted arcuate notch on the upper housing half 16 (not shown) to provide for the same function and geometry for the evacuation control valve actuator button 62. The mated combination of the interrupted arcuate notch 116 of the upper housing half 16 with the interrupted arcuate notch 114 of the lower housing half 18, as well as like structure associated with the interrupted arcuate notch 118, provides for sheltered and recessed locations for protected housing of the inflation control valve actuator button 50 and the evacuation control valve actuator button 62. The location of the inflation control valve actuator button 50 and the evacuation control valve actuator button 62 within the mated combination of the interrupted arcuate notch 116 of the upper housing half 16 with the interrupted arcuate notch 114 of the lower housing half 18, as well as like structure associated with the interrupted arcuate notch 118, requires that wanted depression of the inflation control valve actuator button 50 or the evacuation control valve actuator button 62 can only occur when needed by the operator in that the operator must make a conscious decision and dedicated effort to depress such actuator buttons. Inadvertent actuation of the inflation control valve actuator button 50 or the evacuation control valve actuator button 62 is minimized by the recessed structure surrounding the inflation control valve actuator button 50 and the evacuation control valve actuator button 62.

The upper housing half 16 includes other features not found on the lower housing half 18, including a centrally located orifice 120 in the upper region for accommodation of the pressure gauge 42, a recess 122 in the upper forward region for accommodation of some parts of the inflation tube sealing mechanism 36, and a slot 124 at the forward edge for accommodation of the portion of the inflation tube sealing mechanism 36 which has the receptor orifice 38. A configured lock 126 is provided for locking of the inflation syringe 22 to prevent inadvertent movement of the inflation syringe 22 to preclude inadvertent inflation of an inflatable balloon attached as part of the invention.

FIG. 3 is a view of the internal mechanism assembly 20 prior to installation between the upper housing half 16 and the lower housing half 18. Shown in particular in the illustration are components not previously described or shown or components previously partially shown, now shown for completeness, including the evacuation control valve 60 and the evacuation control valve actuator button 62, Luer connector check valve 58 connected to the evacuation control valve 60, a female Luer lock tee 57 connecting Luer connector check valve 58 to the distal end of the evacuation syringe 28, and a Luer connector purge check valve 130 connected by a flexible plastic tube 132 and connectors 131 and 135 to the central portion of the female Luer lock tee 57. Also shown at the distal end of the four-port infusion "Y" 44 is a Luer connector 133 of the four-port infusion "Y" 44 connected to a female slip Luer 134, and a flexible plastic tube 138 which is, in turn, attached to the pressure gauge 42 by a male slip Luer 136. Arrows 140 and 142 indicate the direction of reorientation of the components proximal to the flexible plastic tubes 54 and 66 about the flexible plastic tubes 54 and 66 when installed between the upper housing half 16 and the lower housing half 18, such as shown in FIGS. 1 and 4.

Figure 5:
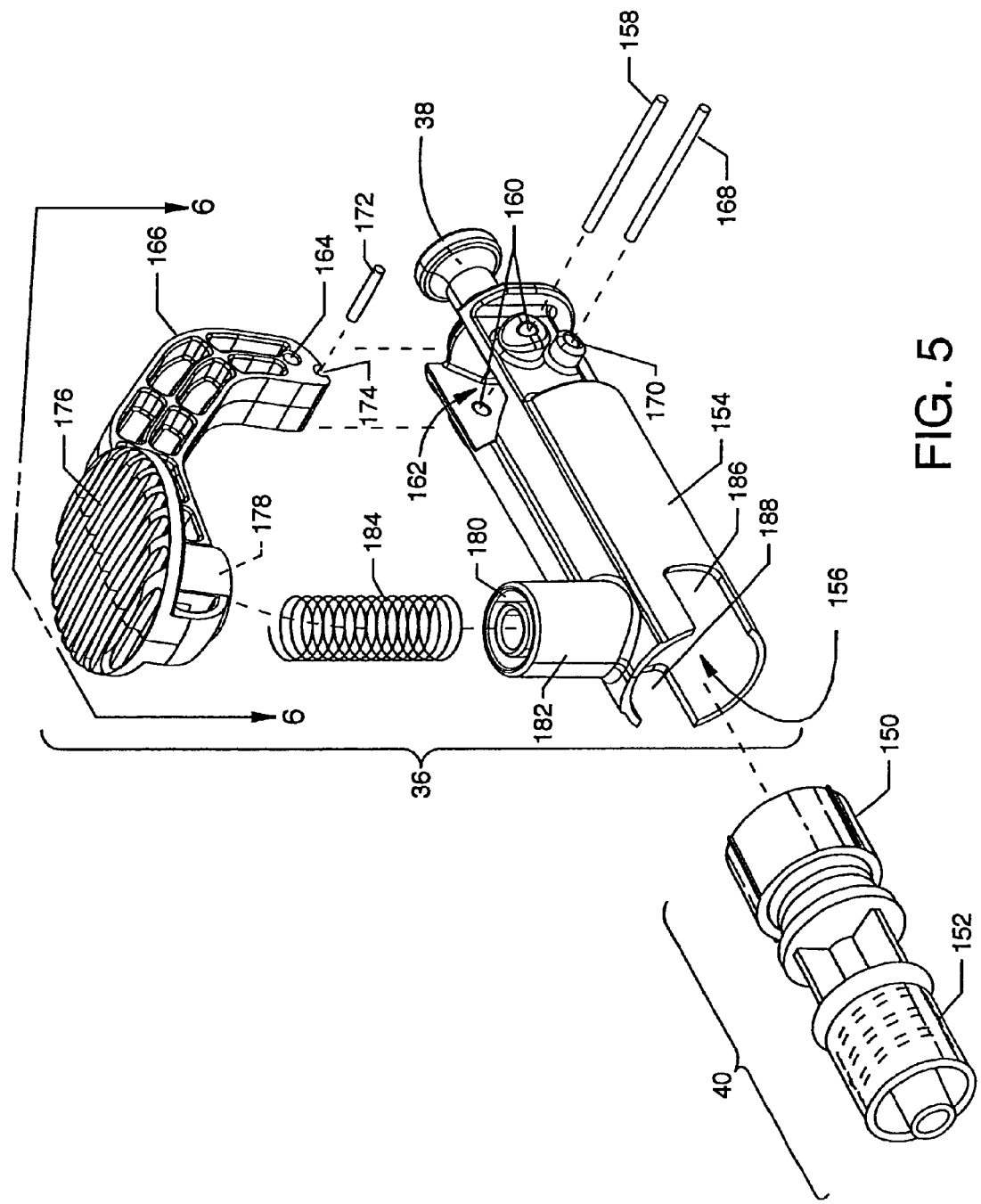
FIG. 5 is an isometric view of the compression sealing mechanism and, in alignment, an exploded isometric view of the inflation tube sealing mechanism.
Figure 6:
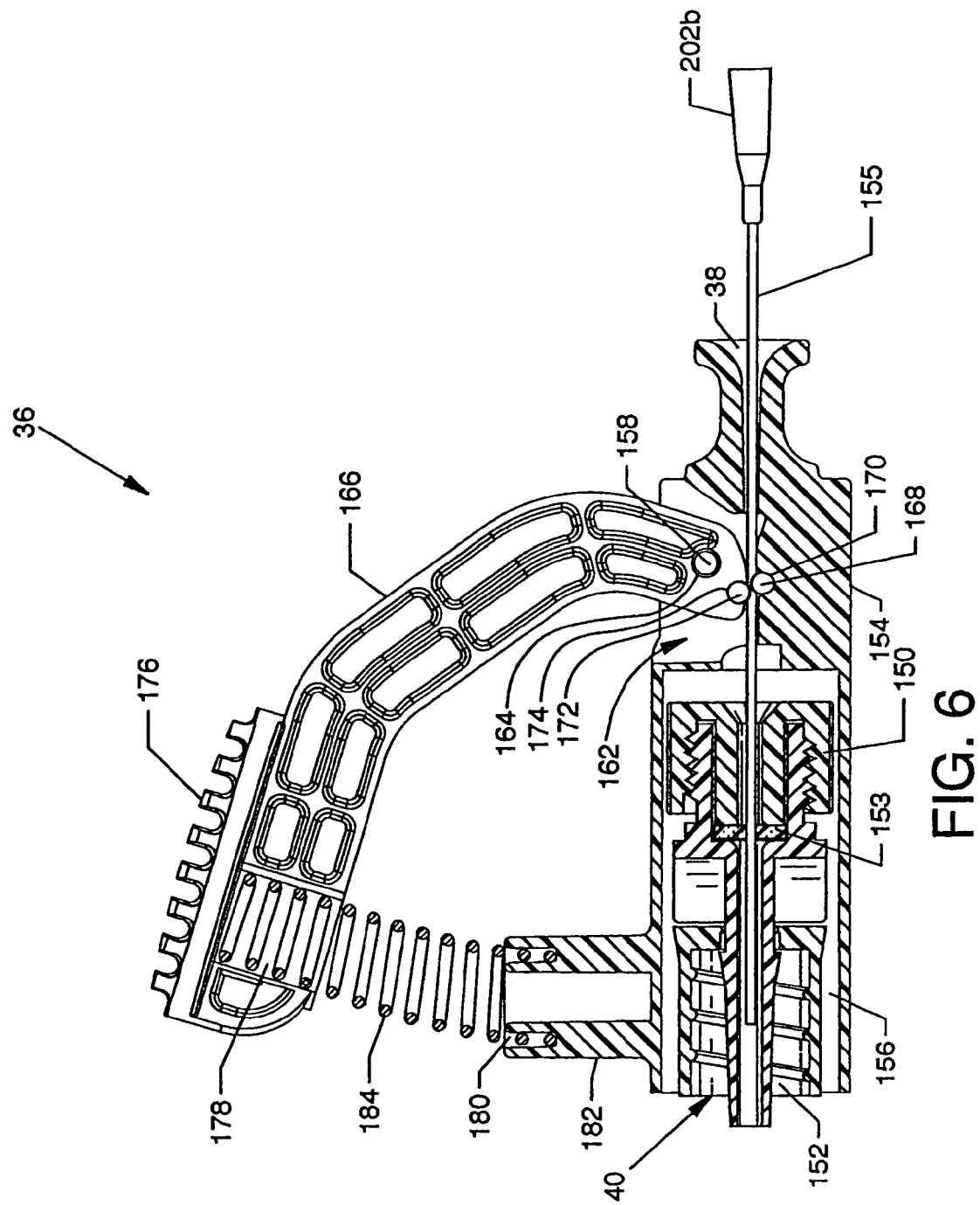
FIG. 6 is a cross section view of the inflation tube sealing mechanism along line 6-6 of FIG. 5.

FIG. 5 is an isometric view of the compression sealing mechanism 40 and, in alignment, an exploded isometric view of the inflation tube sealing mechanism 36. The compression sealing mechanism 40 and the inflation tube sealing mechanism 36 are closely related to patent application Ser. No. 10/838,464 entitled "Gas Inflation/Evacuation System and Sealing System Incorporating a Compression Sealing Mechanism for Guidewire Assembly Having Occlusive Device" filed on May 4, 2004, which is hereby incorporated herein in its entirety by reference, and application Ser. No. 10/838,468 entitled "Guidewire Assembly Including a Repeatably Inflatable Occlusive Balloon on a Guidewire Ensheathed with a Spiral Coil" filed on May 4, 2004, which is hereby incorporated herein in its entirety by reference. The compression sealing mechanism 40 is also referred to and closely related to patent application Ser. No. 10/930,528 entitled "Low Pierce Force Needle Port" filed on Aug. 31, 2004, which is hereby incorporated herein in its entirety by reference. FIG. 6 is a cross section view of the inflation tube sealing mechanism 36 along line 6-6 of FIG. 5.

The compression sealing mechanism 40 includes a sealing cap 150 and a male Luer connector 152. Interior components of the compression sealing mechanism 40 include a puncturable self-sealing seal 153 which seals against the outer surface of a crimpable inflation tube, such as a crimpable inflation tube 155 of FIG. 1.

The inflation tube sealing mechanism 36 includes a configured body 154 being generally tubular in shape and including a passageway 156 for mated accommodation of the sealing cap 150 of the compression sealing mechanism 40 therein. Also included is a pivot dowel pin 158, preferably of hardened steel, which aligns through a hole set 160 in the body 154 and through a cavity 162 in the body 154. The cavity extends along and across one end of the body 154 for accommodation of the lower end of a geometrically configured pivotable handle 166 as well as for accommodation of the pivot dowel pin 158, which extends through a horizontally oriented pivot hole 164 located in the lower region of the pivotable handle 166. A stationary pincer dowel pin 168, preferably of hardened steel, aligns in a transversely oriented hole 170, the central part of which is truncated, the truncated central part being located at the bottom of the cavity 162. The upper region of the stationary pincer dowel pin 168 protrudes slightly above the lower surface of the cavity 162, as shown in FIG. 6, in order to accommodate a surface of the crimpable inflation tube 155. An actuatable pincer dowel pin 172, preferably of hardened steel, aligns and affixes within a truncated hole 174 at the lower region of the handle 166 and protrudes slightly below the lower surface of the lower region of the handle 166. An actuator pad 176, preferably having a tactile surface, is located at the upper end of the handle 166 in close proximity to a spring receptor cavity 178. Another spring receptor cavity 180, which is annular in shape, is located in a cylindrical post 182 extending in vertical orientation from the end of the body 154. Opposing ends of a return spring 184 mount in and between the spring receptor cavity 178 and the spring cavity 180 to position the handle 166 in an open position with respect to the actuatable pincer dowel pin 172 and the stationary pincer dowel pin 168 for accommodation of the crimpable inflation tube 155. Horizontally opposed notches 186 and 188 are located in one end of the body 154 to accommodate other structure of the internal mechanism assembly 20, such as structure of the four-port infusion "Y" 44. The handle 166 is operated about the pivot dowel pin 158 to forcefully urge the actuatable pincer dowel 172 with sufficient force against the crimpable inflation tube 155 and the underlying stationary pincer dowel pin 168 to simultaneously seal and sever the crimpable inflation tube 155. Such action maintains pressure in the severed distal portion of the crimpable inflation tube 155, thereby maintaining inflation of a balloon 210, as later described in detail.

Figure 7:
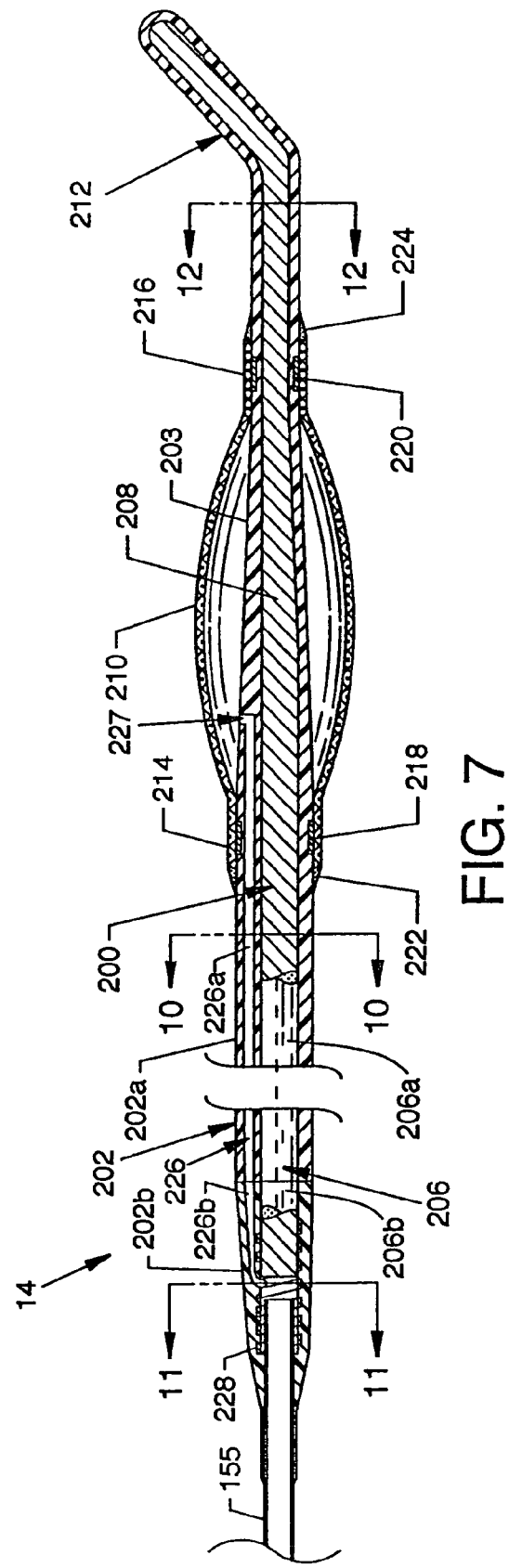
FIG. 7 is a foreshortened cross section view of the torqueable kink-resistant guidewire.
Figure 8:
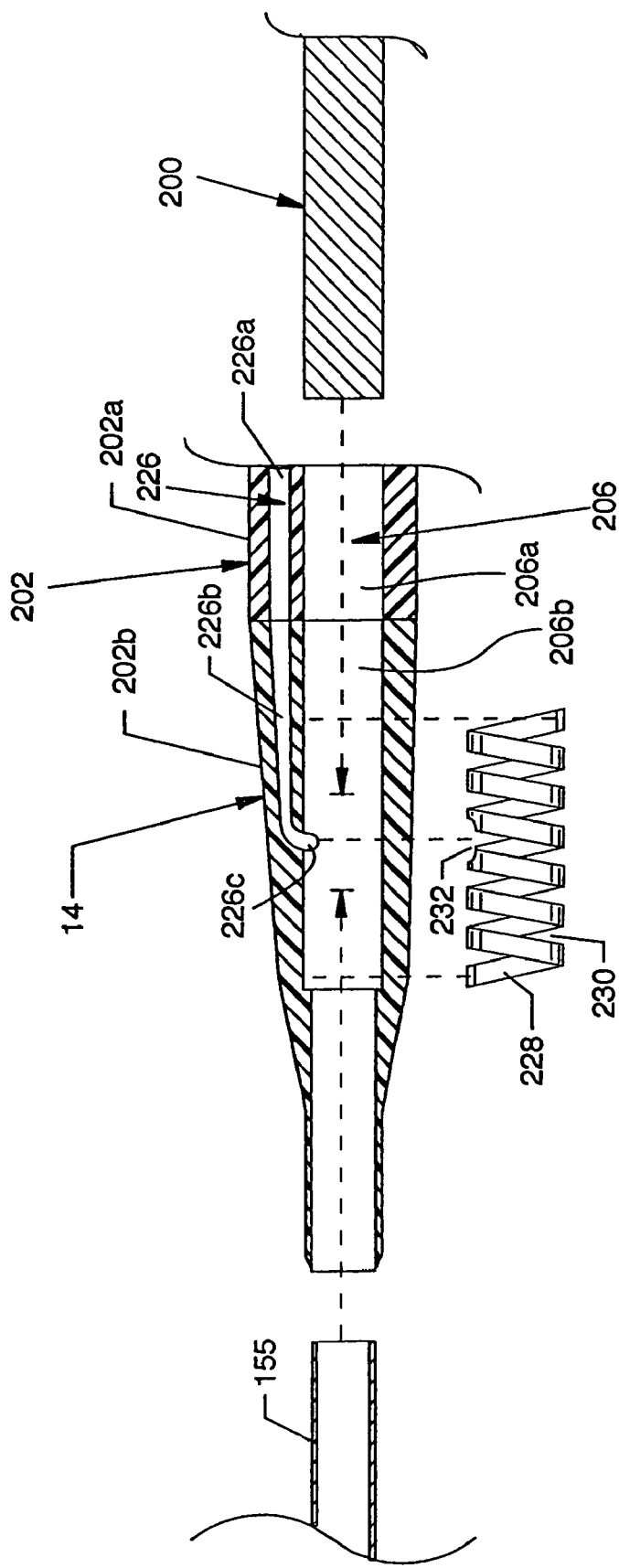
FIG. 8 is an exploded view in partial cross section of the proximal end of the torqueable kink-resistant guidewire.

FIG. 7 is a foreshortened cross section view of the torqueable kink-resistant guidewire 14 for use with the handheld control mechanism 12 of FIG. 1 or other such devices having inflation tube crimping capabilities. FIG. 8 is an exploded view in partial cross section of the proximal end of the torqueable kink-resistant guidewire 14 showing a spiral cut tube 228 which forms a part thereof distanced from the structure of the proximal end of the torqueable kink-resistant guidewire 14. Central to the torqueable kink-resistant guidewire 14 is a shaft 200 composed of nitinol or other suitable material located along and within, and being surrounded by, an elongated polymer jacket section 202a and a short polymer jacket section 202b, the elongated polymer jacket section 202a being joiningly connected to the short polymer jacket section 202b, such as by heat treatment, adhesive or other suitable method, to form a continuous polymer jacket 202. The shaft 200 frictionally and adhesively engages and extends and seals within and along a centrally located lumen section 206a in the elongated polymer jacket section 202a and within and along a centrally located lumen section 206b in the short polymer jacket section 202b, the centrally located lumen sections 206a and 206b being sealingly and unitarily connected and joined to provide a continuous lumen 206 for accommodation of the shaft 200. The shaft 200 includes a tapered section 208 and the elongated polymer jacket section 202a includes a tapered section 203, one or both beginning at or a short distance proximal to the proximal end of a balloon 210 and extending as tapered shapes through the balloon 210 until exiting the balloon 210, whereupon the shaft 200 and the surrounding elongated polymer jacket section 202a can continue as a taper or can continue with a constant radius to then be angled from the centerline of the shaft 200 to form a flexible angled tip 212. Alternatively, the flexible angled tip 212 can be a preshaped polymer tip, a shapeable polymer tip, a preshaped coil tip, or a shapeable coil tip. The balloon 210 can be made from many different materials which may be noncompliant, semi-compliant, or compliant, such as silicone, Pebax, polyurethane, or other suitable material. The balloon 210 includes proximal and distal shoulders 214 and 216 which are annular which secure and seal in a suitable fashion to the elongated polymer jacket section 202a, such as by, but not limited to, the use of heat bonding, adhesive, or other suitable methods. Radiopaque marker bands 218 and 220 are located around and about the elongated polymer jacket section 202a and under the proximal and distal shoulders 214 and 216 of the balloon 210, but may be located at other locations, as required. An adhesive transition fill 222 is incorporated between the edge of the proximal shoulder 214 and the polymer jacket section 202a, and an adhesive transition fill 224 is incorporated between the edge of the distal shoulder 216 and the elongated polymer jacket section 202a. A hydrophilic coating (not shown) is applied over and about the elongated and short polymer jacket sections 202a and 202b which form the polymer jacket 202.

An inflation lumen section 226a within the elongated polymer jacket section 202a and an inflation lumen section 226b within the short polymer jacket section 202b are joined together to form an inflation lumen 226 of continuous nature for inflation of the balloon 210, such inflation lumen 226 extending from and through the short polymer jacket section 202b and through the elongated polymer jacket section 202a to communicatingly exit the elongated polymer jacket section 202a at an inflation port 227 within the interior of the balloon 210.

FIG. 8 illustrates the short polymer jacket section 202b and a portion of the elongated polymer jacket section 202a including structure providing for joining the short polymer jacket section 202b with the shaft 200, the same structure also facilitating communication within the short polymer jacket section 202b between the inflation lumen section 226b, and thus the entire inflation lumen 226, and the crimpable inflation tube 155, which is secured to and within the surrounding proximal portion of the short polymer jacket section 202b. One such structure facilitating communication is a spiral cut tube 228 of stainless steel or other suitable material having one or more cut gaps or spaces such as a continuous spiral space 230 aligned along the body of the spiral cut tube 228. A proximal and arcuate portion 226c of the inflation lumen section 226b communicates through the continuous spiral space 230 of the spiral cut tube 228 with the lumen section 206b. A cutout 232 is also included between adjacent sections of the winding of the spiral cut tube 228 to facilitate communication therethrough with the lumen section 206b.

Figure 9:
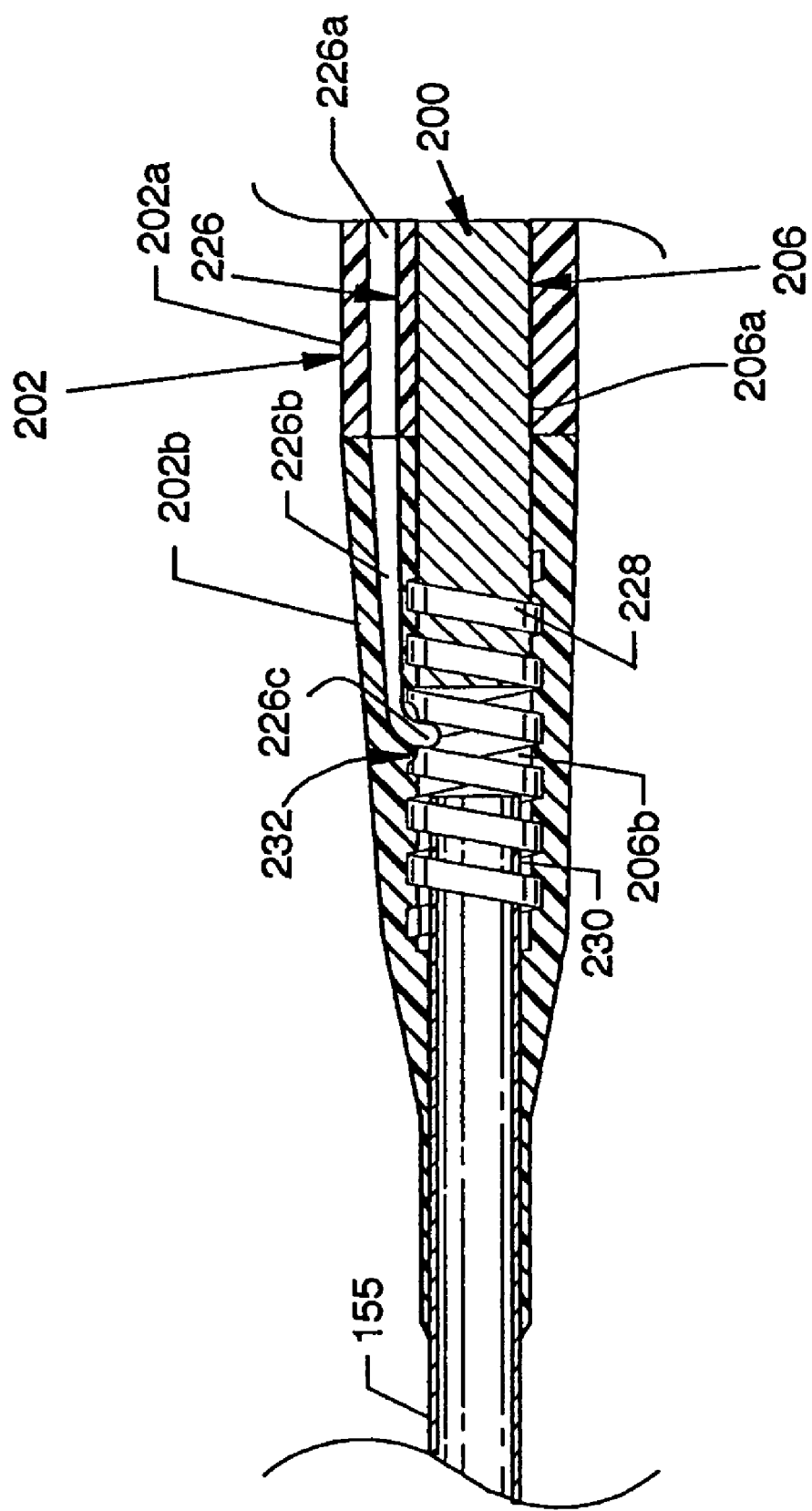
FIG. 9 is an assembled view in partial cross section of the proximal end of the torqueable kink-resistant guidewire shown in FIG. 8.

FIG. 9 is an assembled view in partial cross section of the components of FIG. 8 showing alignment and communication of the arcuate portion 226c of the inflation lumen section 226b with the cutout 232 in the spiral cut tube 228. Communication can also occur at the intersection of the spiral space 230 with the arcuate portion 226c of the inflation lumen section 226b, as the arcuate portion 226c also aligns along a short portion of the lumen section 206b. The distal end of the crimpable inflation tube 155 is located in close proximity to the junction of the arcuate portion 226c of the inflation lumen 226b, the spiral cut tube 228 and the lumen section 206b. The proximal end of the tube 200 seals along the lumen sections 206b and 206a to preclude distally directed pressurization of the lumen sections 206b and 206a distal to the proximal end of the shaft 200.

Figure 10:
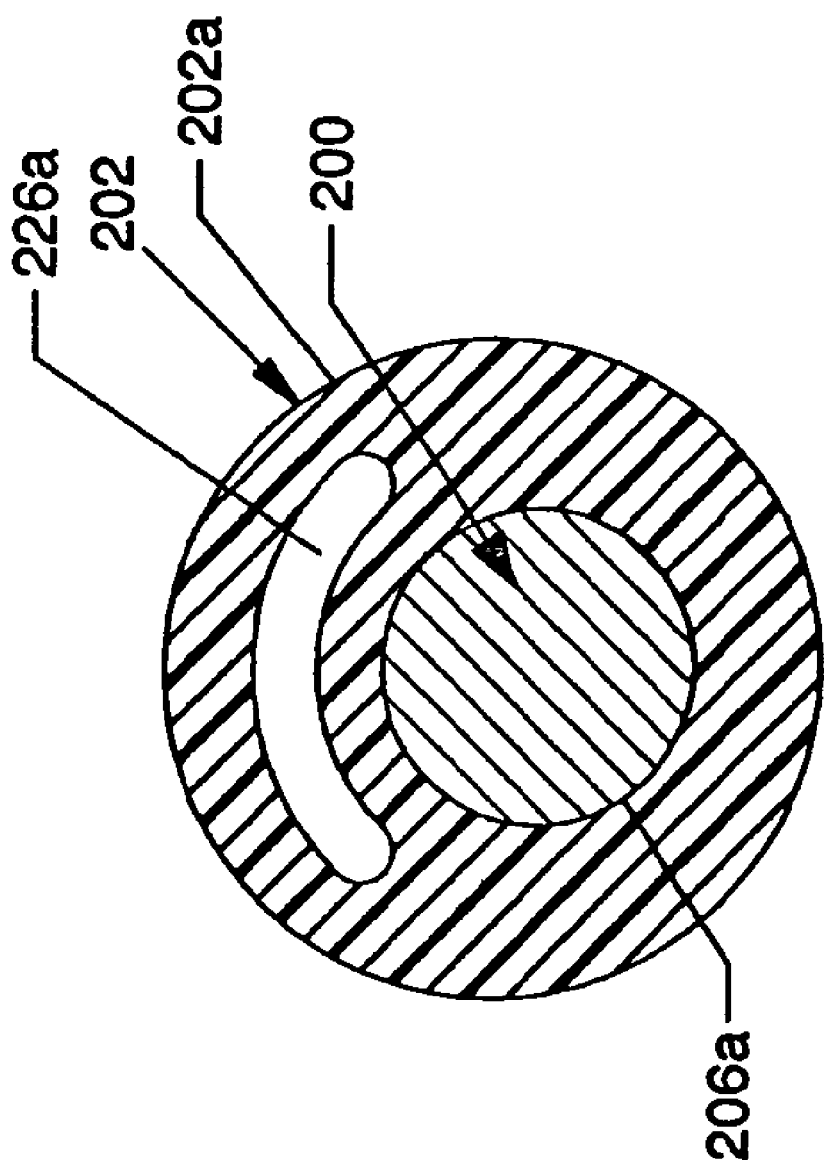
FIG. 10 is a cross section view of the proximal end of the elongated polymer jacket section along line 10-10 of FIG. 7.

FIG. 10 is a cross section view of the proximal end of the elongated polymer jacket section 202a along line 10-10 of FIG. 7.

Figure 11:
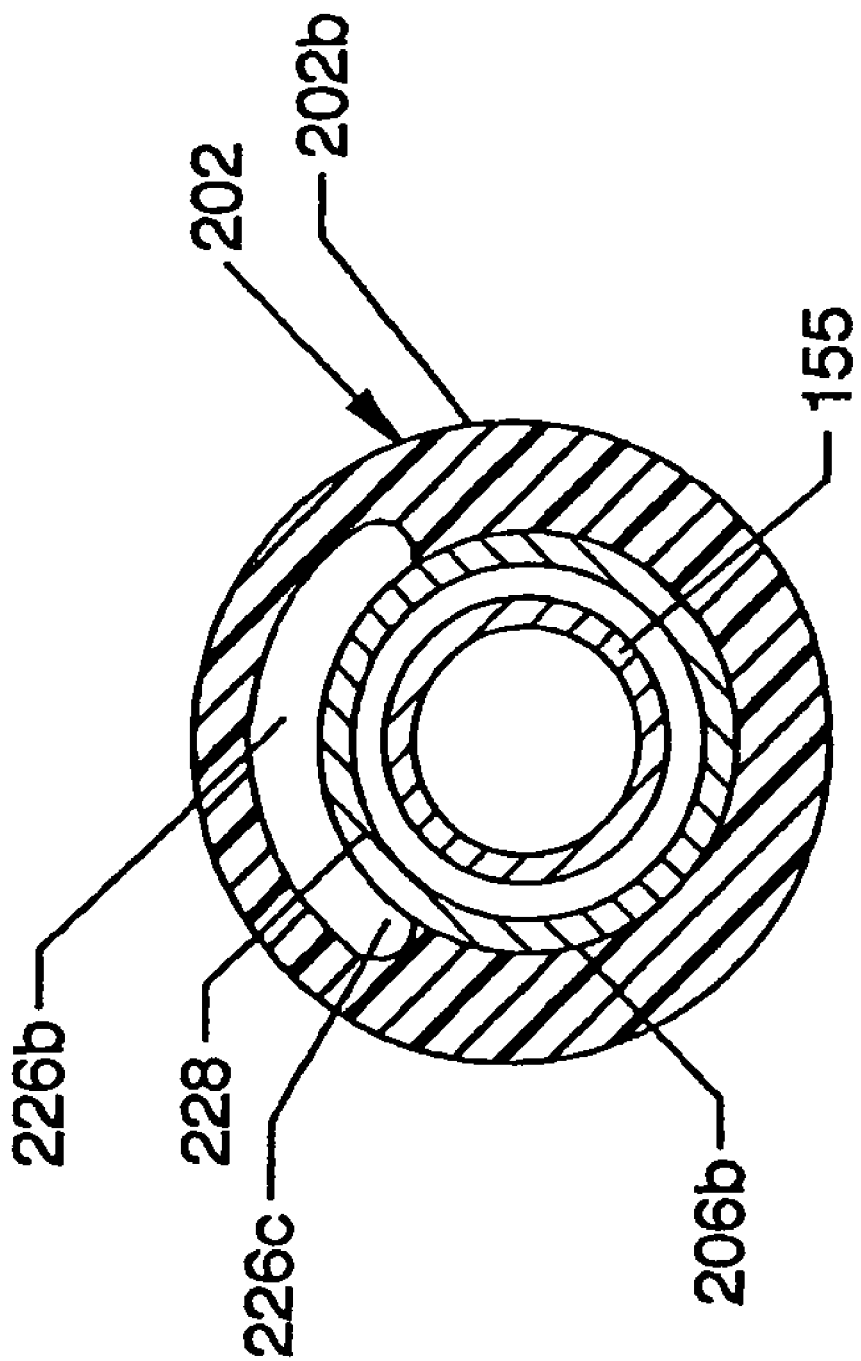
FIG. 11 is a cross section view of the proximal end of the short polymer jacket section along line 11-11 of FIG. 7; and, FIG. 12 is a cross section view of the elongated polymer jacket section and shaft along line 12-12 of FIG. 7.

FIG. 11 is a cross section view of the proximal end of the short polymer jacket section 202b along line 11-11 of FIG. 7.

Figure 12:
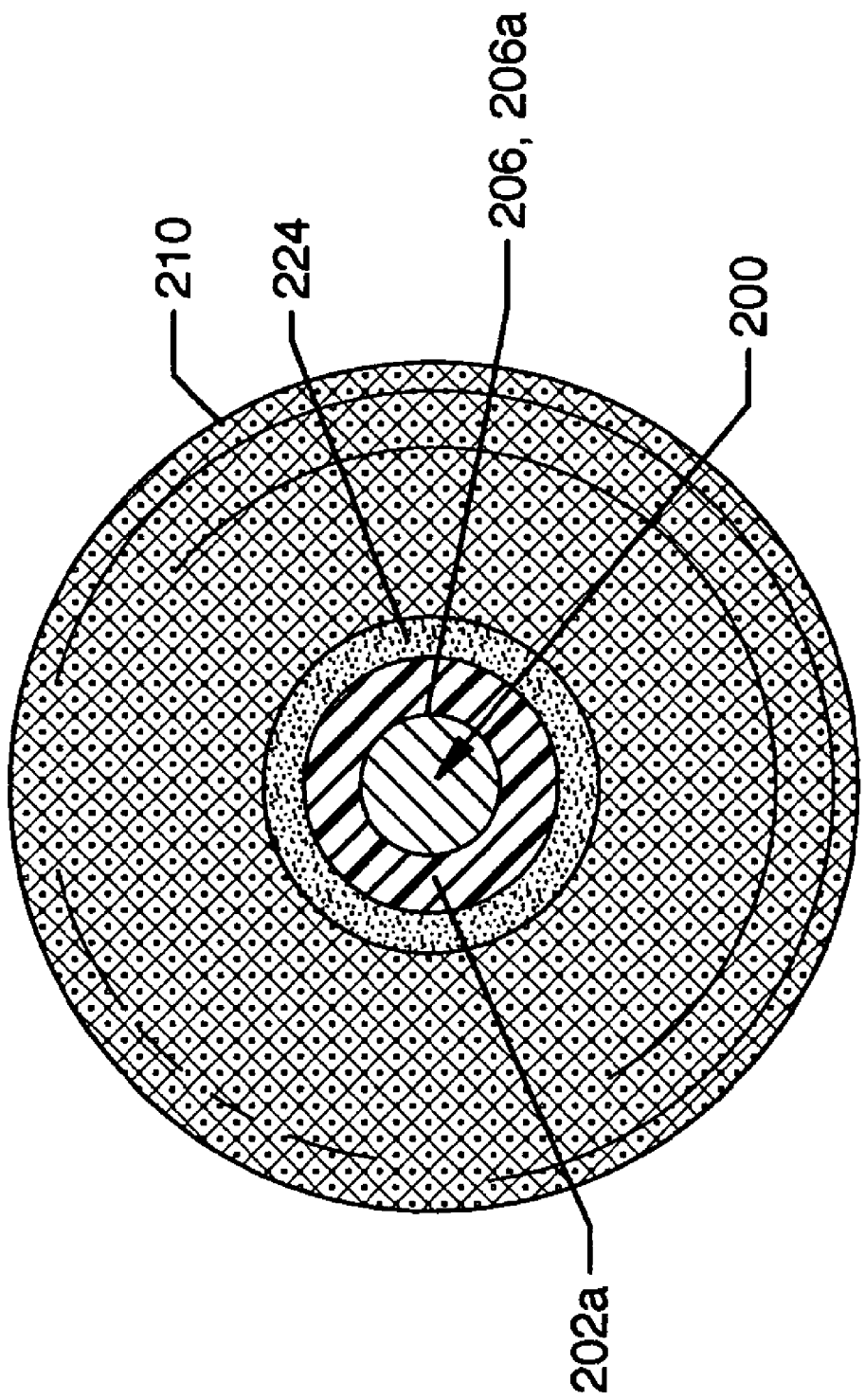

FIG. 12 is a cross section view of the elongated polymer jacket section 202a and shaft 200 along line 12-12 of FIG. 7.

Mode of Operation

Prior to use of the invention, a pressure check (leak test) of the handheld control mechanism 12 is accomplished where such a test very nearly replicates the operation of the invention when incorporating the torqueable kink-resistant guidewire 14. With the torqueable kink-resistant guidewire 14 disengaged from the handheld control mechanism 12, the operator:

1. positions the thumb of the left hand on the evacuation control valve actuator button 62;
2. positions the index finger of the right hand in the actuator ring 32 of the evacuation syringe 28;
3. depresses and holds the evacuation control valve actuator button 62 to open the evacuation control valve 60;
4. uses the index finger of the right hand to outwardly position the actuator ring 32 and attached plunger 30 to evacuate the four-port infusion "Y" 44 and appropriate connected tubes, passages and the like until a zero or less ATM is read on the pressure gauge 42;
5. completely releases pressure on the evacuation control valve actuator button 62 to allow closure of the evacuation control valve actuator 60;

6. removes the index finger from the actuator ring 32 to allow free floating of the evacuation syringe 28, while observing the pressure gauge 42 for no change in position;
7. places the index finger of the left hand on and depresses the inflation control valve actuator button 50 to open the inflation control valve 48;
8. grasps and actuates the actuator pad 26 and actuates the plunger 24 of the inflation syringe 22 slowly and inwardly to induce $CO_2$ and pressurize the four-port infusion "Y" 44 and appropriate connected tubes, passages and the like to 1.5 ATM as read on the pressure gauge 42;
9. releases the inflation control valve actuator button 50 to close the inflation control valve 48 while checking the pressure gauge 42 for stable and maintained pressure; and,
10. resets for inflation by clearing $CO_2$ and/or air from the four-port infusion "Y" 44 and appropriate connected tubes, passages and the like by depressing the evacuation control valve actuator button 62 to open the evacuation control valve 60, thereby automatically releasing the pressurized gas in the four-port infusion "Y" 44 and appropriate connected tubes, passages and the like, followed by full inward actuation of the plunger 30 of the evacuation syringe 28 to cause the plunger stop 34 to impinge the syringe support bracket 70 of the lower housing half 18 and a corresponding like area on the upper housing half 16 to depressurize and to expel $CO_2$ and/or air through the Luer connector purge check valve 130. This resets the vacuum potential of the evacuation syringe 28.

Subsequent to successfully completing the above steps, the torqueable kink-resistant guidewire 14 operation of the invention is accomplished by joining the handheld mechanism 12 to the torqueable kink-resistant guidewire 14 and then advancing the torqueable kink-resistant guidewire 14 along the vasculature to position the balloon 210 just beyond a region of thrombus, plaque, or other undesirable buildup in the vasculature where a thrombectomy will occur, such as with a cross stream thrombectomy catheter or for placing a stent and/or performing a thrombectomy. Alternatively, the torqueable kink-resistant guidewire 14 can be advanced to the thrombus site and then connected to the handheld mechanism 12. Such connection is made by inserting the crimpable inflation tube 155 of the torqueable kink-resistant guidewire 14 into the receptor orifice 38 of the handheld mechanism 12, as shown in FIG. 6, whereby the crimpable inflation tube 155 passes through and seals within the seal 153 to communicate with the interior of the male Luer connector 152 for communication with the four-port infusion "Y" 44 and the components connected thereto including, but not limited to, the evacuation syringe 28, the evacuation control valve 60, the inflation syringe 22 and the inflation control valve 48.

Thence, continuing with the mode of operation and with the torqueable kink-resistant guidewire 14 engaged with the handheld control mechanism 12, and with the balloon 210 of the torqueable kink-resistant guidewire 14 engaged within the vasculature just beyond the thrombus site, the operator:
a. repeats steps 1-9 above to inflate the balloon 210 thereby causing it to contact the side of the vasculature to cause a temporary occlusion;
b. firmly depresses the actuating pad 176 of the inflation tube sealing mechanism 36 to pinch and sever the crimpable inflation tube 155 to cause sealing of the crimpable inflation tube 155 to maintain pressure in the crimpable inflation tube 155 and in the inflated balloon 210, as well as to cause severing of the sealed crimpable inflation tube 155; and,
c. removes the handheld control mechanism 12 from contact with the sealed and pressurized torqueable kink-resistant guidewire 14 and leaves the torqueable kink-resistant guidewire 14 having the inflated balloon 210 within the vasculature to allow the torqueable kink-resistant guidewire 14 to be used as an ordinary guidewire where a cross stream thrombectomy catheter may be used for a thrombectomy procedure or may be used to block lysins from passage beyond the temporary occlusion at the inflated balloon 210.

Removal of the torqueable kink-resistant guidewire 14 from the vasculature is facilitated by cutting of the proximal portion of the sealed crimpable inflation tube 155 with an appropriate cutting tool, such as an ordinary scissors, to cause deflation of the balloon 210 and by then removing the torqueable kink-resistant guidewire 14 from the vasculature. The balloon 210 can be deflated quicker if the cut crimpable inflation tube 155 is reinserted into the seal 153 and vacuum is reestablished. The torqueable kink-resistant guidewire 14 may then be reused according to the remaining length of the crimpable inflation tube 155 to provide for one or more temporary occlusions within the vasculature.

Various modifications can be made to the present invention without departing from the apparent scope thereof.

It is claimed:
1. A guidewire comprising:
(a) a shaft extending from a proximal end thereof to a distal tip thereof;
(b) a crimpable inflation tube interconnected in series with the proximal end of the shaft and defining a tube lumen section therethrough, the crimpable inflation tube having a proximal portion of sufficient length to enable the tube lumen section to be repeatedly sealed airtight by crimping said proximal portion separately at each of a plurality of successive locations therealong and to be repeatedly reopened thereafter by severing said proximal portion just distal to each such location where so crimped to reopen the tube lumen section;
(c) a polymer jacket formed around a predetermined length of the shaft and at least a distal portion of the crimpable inflation tube; the polymer jacket defining within itself an inflation lumen section in communication with the tube lumen section of the crimpable inflation tube; and
(d) a balloon secured about the polymer jacket proximal to the distal tip of the shaft, the balloon having proximal and distal shoulders fixed to and sealed against the polymer jacket on opposite sides of an inflation port defined in the polymer jacket, with the inflation lumen section and the inflation port of the polymer jacket and the tube lumen section of the crimpable inflation tube forming an inflation lumen of the guidewire through which the balloon is capable of being inflated and deflated from a proximal end of the crimpable inflation tube.
2. The guidewire of claim 1 wherein the shaft is made of a super-elastic material.
3. The guidewire of claim 2 wherein the super-elastic material includes nitinol.
4. The guidewire of claim 1 wherein the predetermined length of the shaft is the entirety of the shaft.
5. The guidewire of claim 1 wherein the shaft and the polymer jacket therearound has a tapered section extending distally from approximate the proximal shoulder of the balloon.

6. The guidewire of claim 1 wherein the distal tip of the shaft is angled in a fixed position relative to a centerline of the shaft.

7. The guidewire of claim 1 wherein the distal tip of the shaft has an inner core of nitinol and an outer cover made of at least one of a polymer and a coil, and is thus shapeable relative to a centerline of the shaft.

8. The guidewire of claim 1 wherein the distal tip of the shaft is one of a pre-shaped polymer tip, a shapeable polymer tip, a pre-shaped coil tip and a shapeable coil tip.

9. The guidewire of claim 1 wherein at least one radiopaque marker is located around the polymer jacket approximate the balloon.

10. The guidewire of claim 1 wherein the polymer jacket is coated with a hydrophilic material.

11. The guidewire of claim 1 wherein the polymer of the jacket is loaded with a radiopaque material, the radiopaque material being at least one of tungsten and barium sulfate.

12. The guidewire of claim 1 further including a spiral cut tube for joining the distal portion of the crimpable inflation tube to the proximal end of the shaft.

13. The guidewire of claim 12 the spiral cut tube is coiled about and thereby joins the distal portion of the crimpable inflation tube and the proximal end of the shaft.

14. The guidewire of claim 12 wherein the spiral cut tube defines a continuous spiral space along the length thereof into which the polymer flows as the polymer jacket is formed around the junction of the crimpable inflation tube and the shaft.

15. The guidewire of claim 12 wherein the spiral cut tube is made of stainless steel.

16. The guidewire of claim 1 wherein the balloon is made from at least one of silicone, Pebax and polyurethane.

17. The guidewire of claim 1 wherein the proximal and distal shoulders of the balloon are heat-bonded to the polymer jacket to achieve a minimal profile of the balloon thereupon.

18. A guidewire comprising:
(a) a shaft extending from a proximal end thereof to a distal tip thereof, the shaft defining an inflation lumen section therein;
(b) a crimpable inflation tube interconnected in series with the proximal end of the shaft and defining a tube lumen section therethrough that is in communication with the inflation lumen section of the shaft, the crimpable inflation tube having a proximal portion of sufficient length to enable the tube lumen section to be repeatedly sealed airtight by crimping said proximal portion separately at each of a plurality of successive locations therealong and to be repeatedly reopened thereafter by severing said proximal portion just distal to each such location where so crimped to reopen the tube lumen section;
(c) a polymer jacket formed around a predetermined length of the shaft and at least a distal portion of the crimpable inflation tube; and
(d) a balloon secured about the polymer jacket proximal to the distal tip of the shaft, the balloon having proximal and distal ends sealingly secured to the polymer jacket on opposite sides of an inflation port defined in both the polymer jacket and the shaft through respective sidewalls thereof, with the tube lumen section of the crimpable inflation tube, the inflation lumen section of the shaft and the inflation port defined in both the polymer jacket and the shaft through the respective sidewalls thereof collectively forming an inflation lumen of the guidewire through which the balloon is capable of being inflated and deflated from a proximal end of the crimpable inflation tube.

19. The guidewire of claim 18 wherein the shaft is made of a super-elastic material.

20. The guidewire of claim 19 wherein the super-elastic material includes nitinol.

21. The guidewire of claim 18 wherein the predetermined length of the shaft is the entirety of the shaft.

22. The guidewire of claim 18 wherein the shaft and the polymer jacket therearound has a tapered section extending distally from approximate the proximal shoulder of the balloon.

23. The guidewire of claim 18 wherein the distal tip of the shaft is angled in a fixed position relative to a centerline of the shaft.

24. The guidewire of claim 18 wherein the distal tip of the shaft has an inner core of nitinol and an outer cover made of at least one of a polymer and a coil, and is thus shapeable relative to a centerline of the shaft.

25. The guidewire of claim 18 wherein the distal tip of the shaft is one of a pre-shaped polymer tip, a shapeable polymer tip, a pre-shaped coil tip and a shapeable coil tip.

26. The guidewire of claim 18 wherein at least one radiopaque marker is located around the polymer jacket approximate the balloon.

27. The guidewire of claim 18 wherein the polymer jacket is coated with a hydrophilic material.

28. The guidewire of claim 18 wherein the polymer of the jacket is loaded with a radiopaque material, the radiopaque material being at least one of tungsten and barium sulfate.

29. The guidewire of claim 18 further including a spiral cut tube for joining the distal portion of the crimpable inflation tube to the proximal end of the shaft.

30. The guidewire of claim 29 wherein the spiral cut tube defines a continuous spiral space along the length thereof into which the polymer flows as the polymer jacket is formed around the junction of the crimpable inflation tube and the shaft.

31. The guidewire of claim 29 wherein the spiral cut tube is made of stainless steel.

32. The guidewire of claim 18 wherein the balloon is made from at least one of silicone, Pebax and polyurethane.

33. The guidewire of claim 18 wherein the proximal and distal ends of the balloon are heat-bonded to the polymer jacket to achieve a minimal profile of the balloon thereupon.

* * * * *